(12) United States Patent
Mortara (10) Patent No.: US 6,564,077 B2
(45) Date of Patent: May 13, 2003

(54) METHOD AND APPARATUS FOR PULSE OXIMETRY

(75) Inventor: David W. Mortara, Milwaukee, WI (US)

(73) Assignee: Mortara Instrument, Inc., Milwaukee, WI (US)

(*) Notice: Subject to any disclaimer, the term of this patent is extended or adjusted under 35 U.S.C. 154(b) by 38 days.

(21) Appl. No.: 09/974,279

(22) Filed: Oct. 10, 2001

(65) Prior Publication Data

US 2003/0069487 A1 Apr. 10, 2003

(51) Int. Cl.⁷ .................................................. A61B 5/00
(52) U.S. Cl. ........................................ 600/323; 356/41
(58) Field of Search ................................. 600/310, 322, 600/323, 336; 128/901; 356/41

(56) References Cited

U.S. PATENT DOCUMENTS

| 4,800,495 A | 1/1989 | Smith |
| 4,883,353 A | 11/1989 | Hausman et al. |
| 5,482,036 A | 1/1996 | Diab et al. |
| 5,595,176 A | * 1/1997 | Yamaura .................... 600/323 |

* cited by examiner

Primary Examiner—Eric F. Winakur
Assistant Examiner—David J. McCrosky
(74) Attorney, Agent, or Firm—Patterson, Thuente, Skaar & Christensen, LLC (57) ABSTRACT

An apparatus for determining the oxygenation of blood. The apparatus includes a detector that is configured to sense a first signal of a first wavelength, the first signal having a first arterial blood component and a first noise component. The detector is also configured to sense a second signal of a second wavelength, the second signal having a second arterial blood component and a second noise component. The first arterial blood component is related to the second arterial blood component by an arterial blood absorption ratio and the first noise component is related to the second noise component by a noise absorption ratio. The apparatus also includes a controller that is configured to determine a value of the noise absorption ratio that maximizes the magnitude of an autocorrelation function. The controller is further configured to determine the oxygenation of blood from the noise absorption ratio.

30 Claims, 6 Drawing Sheets

METHOD AND APPARATUS FOR PULSE OXIMETRY

BACKGROUND OF THE INVENTION

1. Field of Invention

The present invention is directed to pulse oximetry. More particularly, the present invention is directed to a method and apparatus for determining oxygen saturation in arterial blood by comparing the absorption of two wavelengths of light.

2. Description of Related Art

Presently, pulse oximetry is used for measuring oxygen saturation in arterial blood by comparing the absorption of signals such as two signals of different wavelengths of light. For example, the absorption of infrared and red light is compared to determine oxygen saturation. Red and infrared light are often used because the relative absorption of these wavelengths is dependent on the relative concentration of oxygenated hemoglobin in blood. According to one arrangement, red and infrared light emitting diodes (LEDs) are placed on one side of a finger and a photo-detector is placed on the opposite side. The red and infrared LEDs are flashed in quick succession and the photo-detector records the amount of light received from each LED in turn. During this process, every normal beat of the heart delivers a pulse of blood throughout the body. The pulse of arterial blood in the capillaries between the LEDs and the photo-detector causes the received levels to vary according to the absorption of the light by the changed path length of the blood through which the light passes. The relative percentage change in the two light levels, expressed as a ratio of the changes of level divided by the ratio of levels, is a characteristic of a particular oxygen saturation, if there are no other sources of variation in absorption.

Thus, pulse oximetry has become a widely used clinical variable. Unfortunately, as the usage has spread to different situations, the accuracy of the underlying assumption that the changes in absorption are due only to pulses of arterial blood has become less reliable. For example, it is now common to monitor oxygen saturation by means of pulse oximetry in both ambulatory patients and infants. In both instances, motion of the patient often creates a motion artifact by introducing changes of the path length of light from the LEDs, which causes changes in the detected light levels. In the absence of a means to distinguish between the changes caused by this motion artifact and the true signal from the pulses of arterial blood, the inferred oxygen saturation becomes unreliable.

Presently, there are methods that attempt to obtain more accurate oxygen saturation measurements than the use of the above process alone. One method is the use of bandpass filtering with conventional pulse oximetry. This method is technologically simple and relatively inexpensive. The use of bandpass filters can be used to reduce some types of artifact. For example, shivering produces artifacts predominantly higher in frequency than the pulse frequency. Thus, low pass filters may help to avoid incorrect results due to shivering patients. Similarly, artifacts of a predominant frequency lower than 0.5 Hz may be reduced by high pass filtering. Unfortunately, the absence of methods to reject more general artifacts causes this type of oximetry method to be either unreliable or unusable in many applications.

Another method for obtaining more accurate oxygen saturation measurements is the use of statistical weighting to reduce the influence of artifacts. In this technique, a measure of noise is used to assign weights to a cluster of saturation measurements with the greatest weight being assigned to the measurements with the smallest noise. This cluster may be derived for either sequential blocks of time, or from multiple spectral components. In cases of intermittent artifacts, statistical weighting can be effective. Unfortunately, if the artifacts are continuous, with no data segment providing a result unaffected by the artifacts, the cumulative result is no better than conventional pulse oximetry.

Another method for obtaining more accurate oxygen saturation measurements is the use of adaptive noise cancellation on the detected signals. Such a method is disclosed in Diab et al., U.S. Pat. No. 5,482,035, issued Jan. 9, 1996, and the corresponding family of patents. Such a method involves generating a reference signal from two detected signals. The reference signal is then used to remove undesired signal portions via an adaptive noise canceler such as a joint process estimator. Unfortunately, this method is expensive and requires a relative large amount of power to operate the required signal processor. Also, this is an indirect method for determining the oxygen saturation. For example, this method must perform additional processing on the signal after canceling the noise to obtain the oxygen saturation.

SUMMARY OF THE INVENTION

The present invention provides a method and apparatus for determining oxygen saturation in arterial blood. The apparatus includes a detector that is configured to sense a first signal of a first wavelength, the first signal having a first arterial blood component and a first noise component. The detector is also configured to sense a second signal of a second wavelength, the second signal having a second arterial blood component and a second noise component. The first arterial blood component is related to the second arterial blood component by an arterial blood absorption ratio and the first noise component is related to the second noise component by a noise absorption ratio. The apparatus also includes a controller that is configured to determine a value of the noise absorption ratio that maximizes the magnitude of an autocorrelation function. The controller is further configured to determine the oxygenation of blood from the noise absorption ratio.

The controller can further be configured to determine the oxygenation of blood by determining the arterial blood absorption ratio from the noise absorption ratio and by determining the oxygenation of blood from the arterial blood absorption ratio. The controller can also be configured to determine the value of the noise absorption ratio by maximizing the magnitude of the autocorrelation function by setting a derivative of the autocorrelation function with respect to the noise absorption ratio to zero.

The controller can additionally be configured to determine the value of the noise absorption ratio by minimizing the mean square of the derivative of the autocorrelation function with respect to the noise absorption ratio and with respect to the arterial blood absorption ratio. The controller can further be configured to determine the value of the noise absorption ratio by determining a normalized autocorrelation function and by determining the value of the noise absorption ratio at a lag where the normalized autocorrelation function reaches a maximum on a specified interval.

The controller can also be configured to determine the normalized autocorrelation function by dividing the autocorrelation function by the autocorrelation function at a time lag of zero to obtain the normalized autocorrelation function. The controller can additionally be configured to determine the value of the noise absorption ratio by determining the best estimate of a pulse-to-pulse interval. The best estimate of a pulse-to-pulse interval can be determined from external information and/or information determined from available pulse oximetry data.

The controller can further be configured to determine the quality of at least one solution of the noise absorption ratio with respect to another solution of the noise absorption ratio based on the highest signal to noise ratio and choose the best solution based on the quality of the solution.

The present invention also provides a pulse oximeter. The pulse oximeter includes a light source configured to provide first signal of a first wavelength and a second signal of a second wavelength. The pulse oximeter also includes a detector configured to sense the first signal of the first wavelength and the second signal of the second wavelength. The first signal has a first arterial blood component and a first noise component and the second signal has a second arterial blood component and a second noise component. The first arterial blood component is related to the second arterial blood component by an arterial blood absorption ratio. Also, the first noise component is related to the second noise component by a noise absorption ratio. The pulse oximeter additionally includes a processor configured to determine a value of the noise absorption ratio that maximizes the magnitude of an autocorrelation function and to determine the oxygenation of blood from the noise absorption ratio.

The processor can further be configured to determine the oxygenation of blood by determining the arterial blood absorption ratio from the noise absorption ratio and by determining the oxygenation of blood from the arterial blood absorption ratio. The processor can also be configured to determine the value of the noise absorption ratio by maximizing the magnitude of the autocorrelation function by setting a derivative of the autocorrelation function with respect to the noise absorption ratio to zero.

The present invention additionally provides a method for determining the oxygenation of blood. The method includes sensing a first signal of a first wavelength, the first signal having a first arterial blood component and a first noise component, sensing a second signal of a second wavelength, the second signal having a second arterial blood component and a second noise component, the first arterial blood component being related to the second arterial blood component by an arterial blood absorption ratio and the first noise component being related to the second noise component by a noise absorption ratio, determining a value of the noise absorption ratio that maximizes the magnitude of an autocorrelation function, and determining the oxygenation of blood from the noise absorption ratio.

The determining the oxygenation of blood step can also include determining the arterial blood absorption ratio from the noise absorption ratio, and determining the oxygenation of blood from the arterial blood absorption ratio. The determining the value of the noise absorption ratio step can additionally include maximizing the magnitude of the autocorrelation function by setting a derivative of the autocorrelation function with respect to the noise absorption ratio to zero.

The determining the value of the noise absorption ratio step can further include determining the value of the noise absorption ratio by minimizing the mean square of the derivative of the autocorrelation function with respect to the noise absorption ratio and with respect to the arterial blood absorption ratio. The determining the value of the noise absorption ratio step can also include determining a normalized autocorrelation function and determining the value of the noise absorption ratio at a lag where the normalized autocorrelation function reaches a maximum on a specified interval.

The determining the normalized autocorrelation function can include dividing the autocorrelation function by the autocorrelation function at a time lag of zero to obtain the normalized autocorrelation function. The determining the value of the noise absorption ratio step can further include determining the best estimate of a pulse-to-pulse interval. The best estimate of a pulse-to-pulse interval can be determined from at least one of external information and information determined from available pulse oximetry data.

The method for determining the oxygenation of blood can additionally include determining the quality of at least one solution of the noise absorption ratio with respect to another solution of the noise absorption ratio based on the highest signal to noise ratio and choosing the best solution based on the quality of the solution.

The present invention additionally provides a method for determining the oxygenation of blood including the steps of transmitting a signal through a medium containing blood, sensing a first signal of a first wavelength, the first signal having a first arterial blood component and a first noise component, sensing a second signal of a second wavelength, the second signal having a second arterial blood component and a second noise component, the first arterial blood component being related to the second arterial blood component by an arterial blood absorption ratio and the first noise component being related to the second noise component by a noise absorption ratio, determining a value of the noise absorption ratio that maximizes the magnitude of an autocorrelation function, and determining the oxygenation of blood from the noise absorption ratio.

The method can also include the steps of determining the quality of at least one solution of the noise absorption ratio with respect to another solution of the noise absorption ratio based on the highest signal to noise ratio and choosing the best solution based on the quality of the solution. The at least one solution can include a method including the step of minimizing a mean square of the autocorrelation function and the another solution can include a method including the step of normalizing the autocorrelation function. The at least one solution can also include a method including the step of minimizing a mean square of the autocorrelation function and the another solution can include a method including the step of determining the best estimate of a pulse-to-pulse interval. The at least one solution can further include a method including the step of normalizing the autocorrelation function and the another solution can include a method including the step of determining the best estimate of a pulse-to-pulse interval. The at least one solution can be selected from a set of methods including a method including the step of determining the best estimate of a pulse-to-pulse interval, a method including the step of normalizing the autocorrelation function, and a method including the step of minimizing a mean square of the autocorrelation function.

BRIEF DESCRIPTION OF THE DRAWINGS

The preferred embodiments of the present invention will be described with reference to the following figures, wherein like numerals designate like elements, and wherein.

DETAILED DESCRIPTION OF PREFERRED EMBODIMENTS

Figure 1:
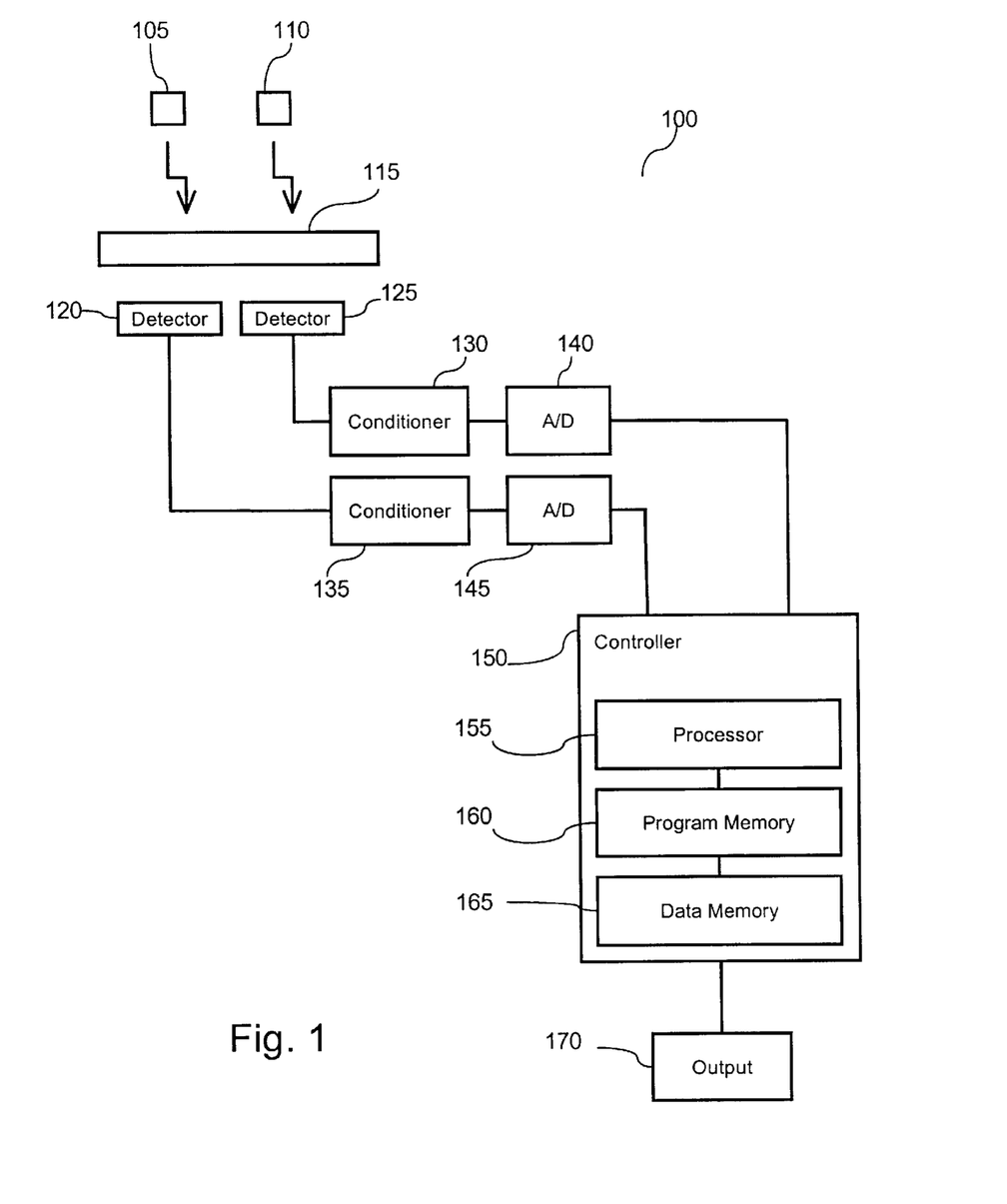
FIG. 1 is an exemplary block diagram of a system according to one embodiment.

FIG. 1 is an exemplary block diagram of a system 100 according to one embodiment. The system 100 includes transmitters 105 and 110, transmission medium 115, detectors 120 and 125, signal conditioners 130 and 135, analog to digital (A/D) converters 140 and 145, a controller 150, and an output 170. The controller 150 can include a processor 155, and program memory 160, and a data memory 165. The controller 150 may alternatively comprise a digital signal processor or any other device useful for performing controller functions. The transmitters 105 and 110 can be light emitting diodes, red and infrared light transmitters, or any other device used to transmit a useful signal. Also, the transmitters 105 and 110 may be one transmitter or multiple transmitters. The transmission medium may be a finger, an ear, a test tube, or any other medium that can contain blood. The detectors 120 and 125 can be sensors, photodetectors, or any other device used to detect a signal. The detectors 120 and 125 may also be one detector or multiple detectors.

According to one mode of operation, the transmitters 105 and 110 transmit red and infrared light signals through the transmission medium 115. The detectors 120 and 125 detect the signal received from the transmitters 105 and 110 via the transmission medium 115. The resulting signals include a signal due to the transmitted signals and a signal due to noise. Thus, the detectors 120 and 125 sense a first signal of a first wavelength, the first signal having a first arterial blood component and a first noise component. The detectors 120 and 125 also thus sense a second signal of a second wavelength, the second signal having a second arterial blood component and a second noise component. The first arterial blood component is related to the second arterial blood component by an arterial blood absorption ratio and the first noise component is related to the second noise component by a noise absorption ratio. The signals are then sent through conditioners 130 and 135 which perform signal conditioning, gain control, and other conditioning functions. The A/D converters 140 and 145 then perform analog to digital conversion on the signals.

The signals are then sent to the controller 150. The controller 150 is configured to determine a value of a noise absorption ratio of the signals that maximizes the magnitude of an autocorrelation function and to determine the oxygenation of blood from the noise absorption ratio. The controller 150 can further be configured to determine the oxygenation of blood by determining the arterial blood absorption ratio from the noise absorption ratio and by determining the oxygenation of blood from the arterial blood absorption ratio. The controller 150 can also be configured to determine the value of the noise absorption ratio by maximizing the magnitude of the autocorrelation function by setting a derivative of the autocorrelation function with respect to the noise absorption ratio to zero.

The controller 150 can additionally be configured to determine the value of the noise absorption ratio by minimizing the mean square of the derivative of the autocorrelation function with respect to the noise absorption ratio and with respect to the arterial blood absorption ratio. The controller 150 can further be configured to determine the value of the noise absorption ratio by determining a normalized autocorrelation function and by determining the value of the noise absorption ratio at a lag where the normalized autocorrelation function reaches a maximum on a specified interval.

The controller 150 can also be configured to determine the normalized autocorrelation function by dividing the autocorrelation function by the autocorrelation function at a time lag of zero. The controller 150 can additionally be configured to determine the value of the noise absorption ratio by determining the best estimate of a pulse-to-pulse interval. The best estimate of a pulse-to-pulse interval can be determined from external information and/or information determined from available pulse oximetry data. The controller 150 can further be configured to determine the quality of at least one solution of the noise absorption ratio with respect to another solution of the noise absorption ratio based on the highest signal to noise ratio and choose the best solution based on the quality of the solution.

A result from the controller 150 may be sent to the output 170. This result may be a value obtained for the arterial blood absorption ratio, the value obtained for the noise absorption ratio, a value obtained for the oxygen saturation, or any other useful value. The output 170 may be a display for displaying the oxygen saturation of arterial blood. The output 170 may also be a bus or signal line for providing information to other components of a pulse oximetry system. The output 170 may further be a signal line, modem, network bus, or any other output or connection device for providing results obtained from the controller 150 to other devices.

According to another embodiment of operation, the controller 150 determines the oxygenation of blood according to the processes described below. These processes describe the operation of the controller 150 described above in further detail.

Figure 2:
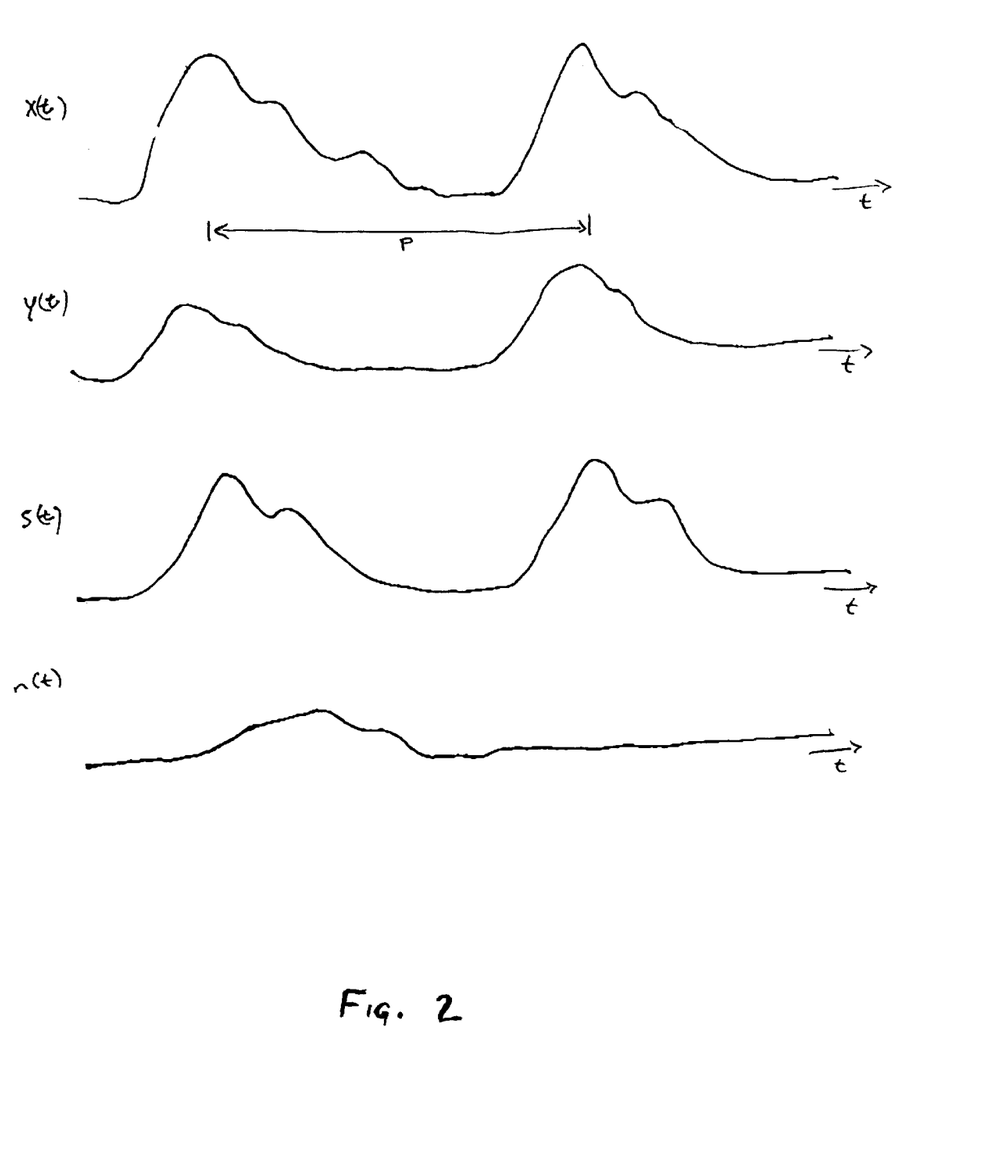
FIG. 2 is an exemplary illustration of signals x(t) and y(t), signal component s(t), and noise component n(t)

The controller 150 can combine signal modeling and statistical weighting concepts. Accordingly, the signal from an infrared transmitter 105 is designated x(t) and the signal from the red transmitter 110 is designated y(t). The signal from each transmitter has a component due to arterial blood, delivered in pulses at the heart rate, and a noise component. Each component has a constant ratio of infrared to red absorption over a short period of time. In algebraic terms, a signal model of x(t) and y(t) is expressed as:

$$x(t)=Rs(t)+rn(t) \qquad (Eq.\ 1)$$

$$y(t)=s(t)+n(t) \qquad (Eq.\ 2)$$

where R is the absorption ratio for the arterial blood, r is the absorption ratio for the noise component, s(t) is the time-dependent red signal from the arterial blood, and n(t) is the red signal from the noise component. The absorption ratio is generally different between the arterial component and the noise component. FIG. 2 is an exemplary illustration of signals x(t) and y(t), signal component s(t), and noise component n(t) with respect to time t. The signals can have a pulse-to-pulse interval P.

These signal model equations can be solved for s(t) and n(t):

$$s(t)=(x(t)-ry(t))/(R-r) \qquad (Eq.\ 3.1)$$

$$n(t)=(x(t)-Ry(t))/(r-R) \qquad (Eq.\ 3.2)$$

Figure 3:
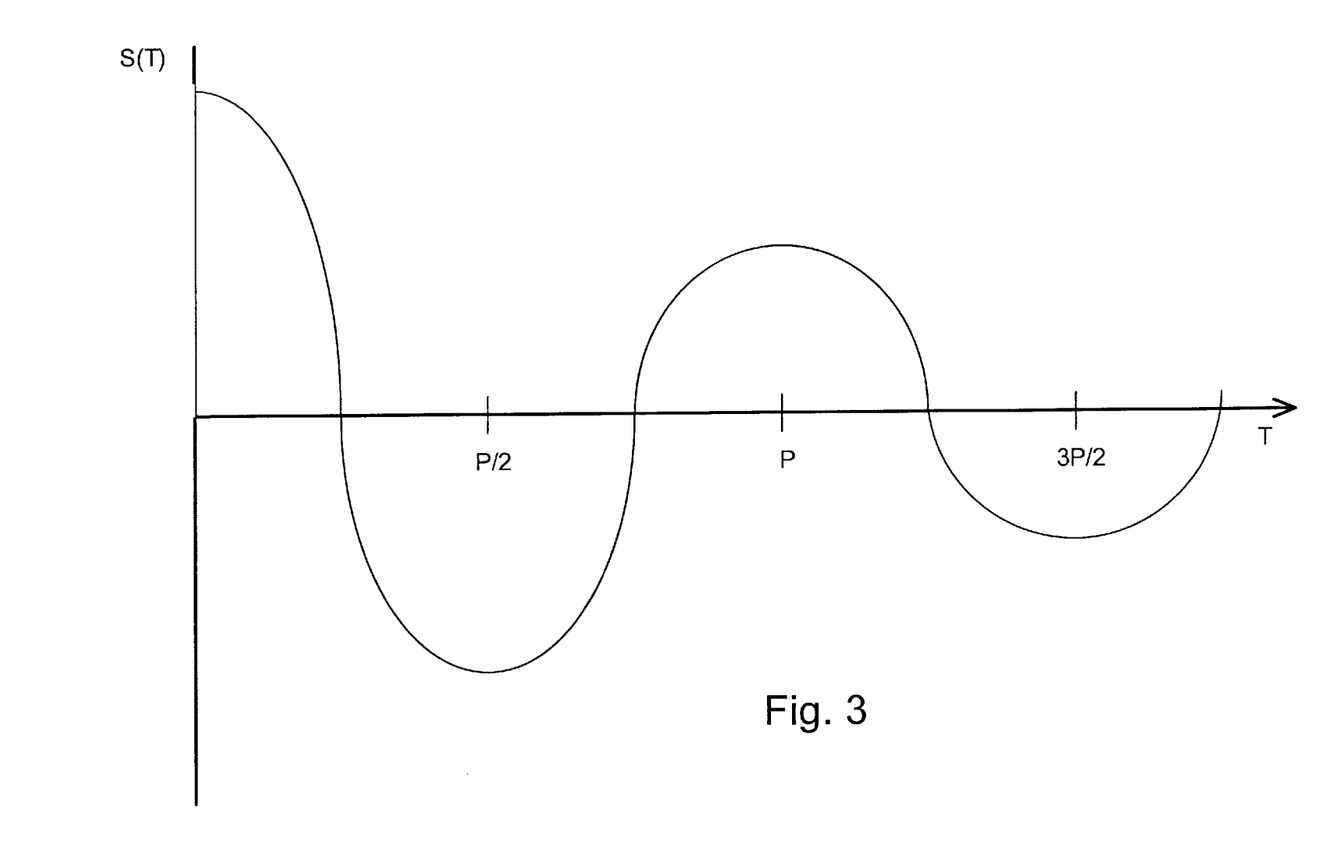
FIG. 3 is an exemplary illustration of the autocorrelation estimate.

The autocorrelation estimate S(T) for time lag T for the signal s(t) is defined as the average value of the product s(t)s(t−T):ps $$S(T)=<s(t)s(t-T)>, \text{ or} \quad \text{(Eq. 3.3)}$$

$$\text{Si } S(T)=<x(t)x(t-T)-r(x(t)y(t-T)-r\ x(t-T)y(t)+ \\ r^2y(t)y(t-T)>/(R-r)^2 \quad \text{(EQ 3.4)}$$

FIG. 3 is an exemplary illustration of the autocorrelation estimate. For simplicity of mathematical manipulations, the following definitions are made:

$$X(T)=<x(t)x(t-T)> \quad \text{(Eq. 4.1)}$$

$$Y(T)=<y(t)y(t-T)> \quad \text{(Eq. 4.2)}$$

$$U(T)=<x(t)y(t-T)+x(t-T)y(t)>/2 \quad \text{(Eq. 4.3)}$$

Then:

$$S(T)=(X(T)-2rU(T)+r^2Y(T))/(R-r)^2 \quad \text{(Eq. 5.1)}$$

Similarly, the noise autocorrelation estimate is:

$$N(T)=(X(T)-2RU(T)+R^2Y(T))/(R-r) \quad \text{(Eq. 5.2)}$$

Figure 4:
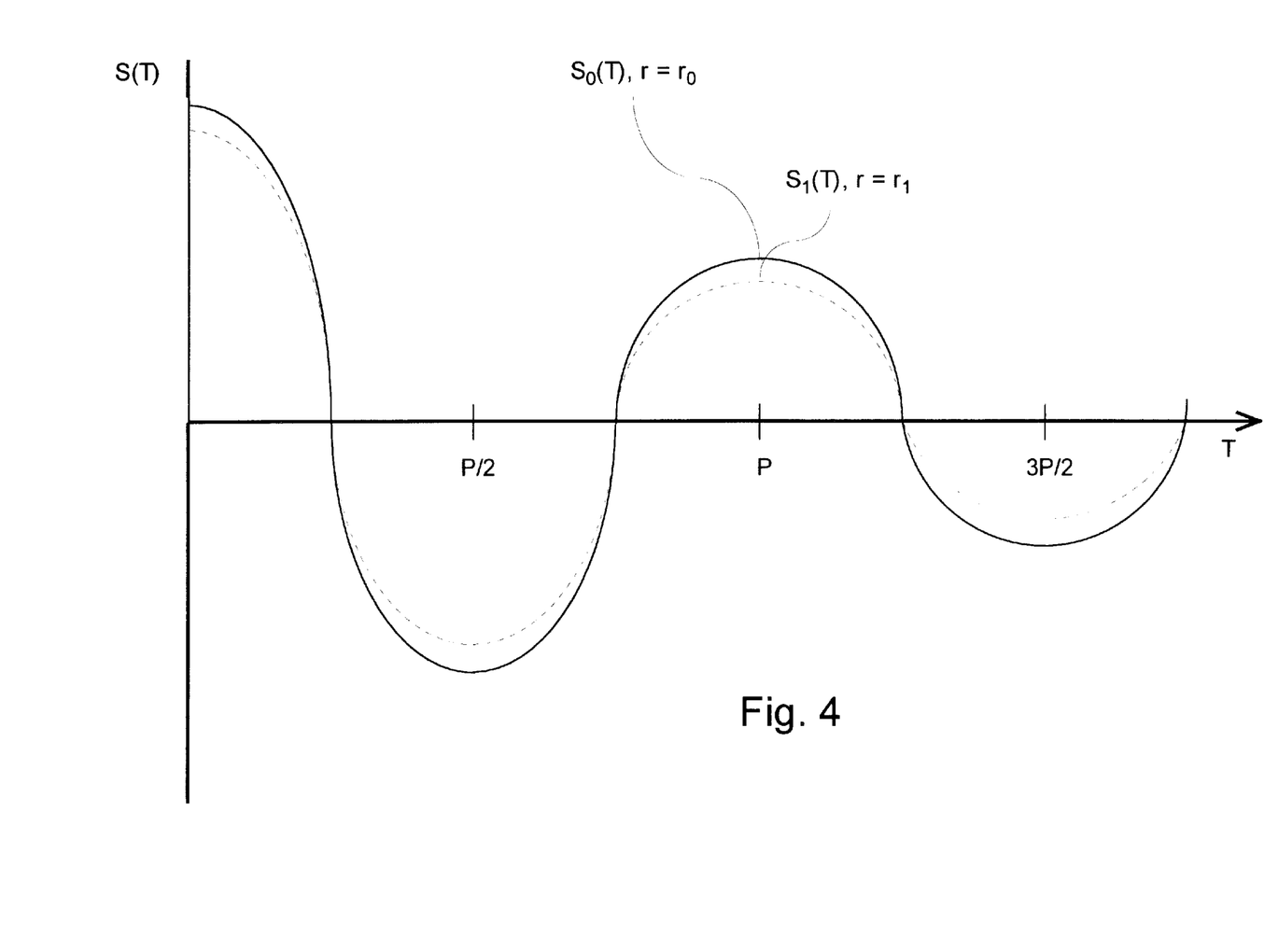
FIG. 4 is an exemplary illustration of the autocorrelation function S(T) for different values of r.

The function S(T), defined for T>=0, has the appearance of a damped sinusoid for the case that s(t) has periodic components. The damping occurs as a result of aperiodic components in the signal s(t). It is important to note that the damping of S(T) may also be due to an incorrect estimate of s(t). Conversely, a correct estimate of the noise absorption ratio is expected to maximize the magnitude of S(T). FIG. 4 is an exemplary illustration of the autocorrelation function S(T) for different values of r. It is desired to obtain the best value of r to give the best autocorrelation estimate S(T). For example, $S_0(T)$ for $r=r_0$ yields a better result than $S_1(T)$ for $r=r_1$. To find the extremum with respect to the noise absorption ratio, the derivative of S(T) is taken with respect to r:

$$dS(T)/dr=2(X(T)-(R+r)U(T)+RrY(T))/(R-r)^3 \quad \text{(Eq. 6)}$$

At an extremum, the derivative is zero, requiring:

$$R=(X(T)-rU(T))/(U(T)-rY(T)) \quad \text{(Eq. 7)}$$

Eq. 7 yields R if r is known. Thus, it is useful to determine the noise absorption ratio in order to determine the arterial blood absorption ratio. Then, the oxygen saturation of blood can be determined, for example, from a look up table, from a chart, or from any other source useful for determining oxygen saturation from the arterial blood absorption ratio. There are at least three different solutions for determining R and r.

A first solution for determining R and r involves recognizing that Eq. 7 is not a single equation, but that it is a relation which is approximately true for all values of T. The derivative of S(T) is made zero in the least square sense by minimizing the mean square of dS(T)/dr with respect to r and R. This results in two equations for R and r, which then have a solution.

For simplicity of mathematical manipulations, the following definitions are made:

$$A=\int X(T)U(T)dT/T_{max} \quad \text{(Eq. 8.1)}$$

$$B=\int U(T)U(T)dT/T_{max} \quad \text{(Eq. 8.2)}$$

$$C=\int Y(T)U(T)dT/T_{max} \quad \text{(Eq. 8.3)}$$

$$D=\int X(T)Y(T)dT/T_{max} \quad \text{(Eq. 8.4)}$$

$$E=\int Y(T)Y(T)dT/T_{max} \quad \text{(Eq. 8.5)}$$

$$F=BE-CC \quad \text{(Eq. 8.6)}$$

$$G=(AC-DB)/F \quad \text{(Eq. 8.7)}$$

$$H=(AE-DD)/F \quad \text{(Eq. 8.8)}$$

The integrals in Eqs. 8.1–8.5 are performed on the interval $[0, T_{max}]$. $T_{max}$ is preferably at least as large as the longest pulse-to-pulse intervals expected. If G>0, the normal solutions for R and r are:

$$R=(H-\sqrt{(HH-4G)})/2 \quad \text{(Eq. 9.1)}$$

$$r=(H+\sqrt{(HH-4G)})/2 \quad \text{(Eq. 9.2)}$$

While for G<0:

$$R=(H+\sqrt{(HH-4G)})/2 \quad \text{(Eq. 9.3)}$$

$$r=(H-\sqrt{(HH-4G)})/2 \quad \text{(Eq. 9.4)}$$

A transform of S(T) may be used in place of S(T). An example would be the Fourier transform, which would replace S(T) by a function of frequency. Similar to the maximization of S(T), the Fourier transform might be maximized as a function of frequency with respect to the noise absorption ratio. Moreover, the transformed function may be determined directly from x(t) and y(t) without explicit determination of S(T).

A second solution is found by considering the normalized signal autocorrelation, S'(T):

$$S'(T)=S(T)/S(0)=(X(T)-2rU(T)+r^2Y(T))/(X(0)-2rU(0)+ \\ r^2Y(0)) \quad \text{(Eq. 10)}$$

Figure 5:
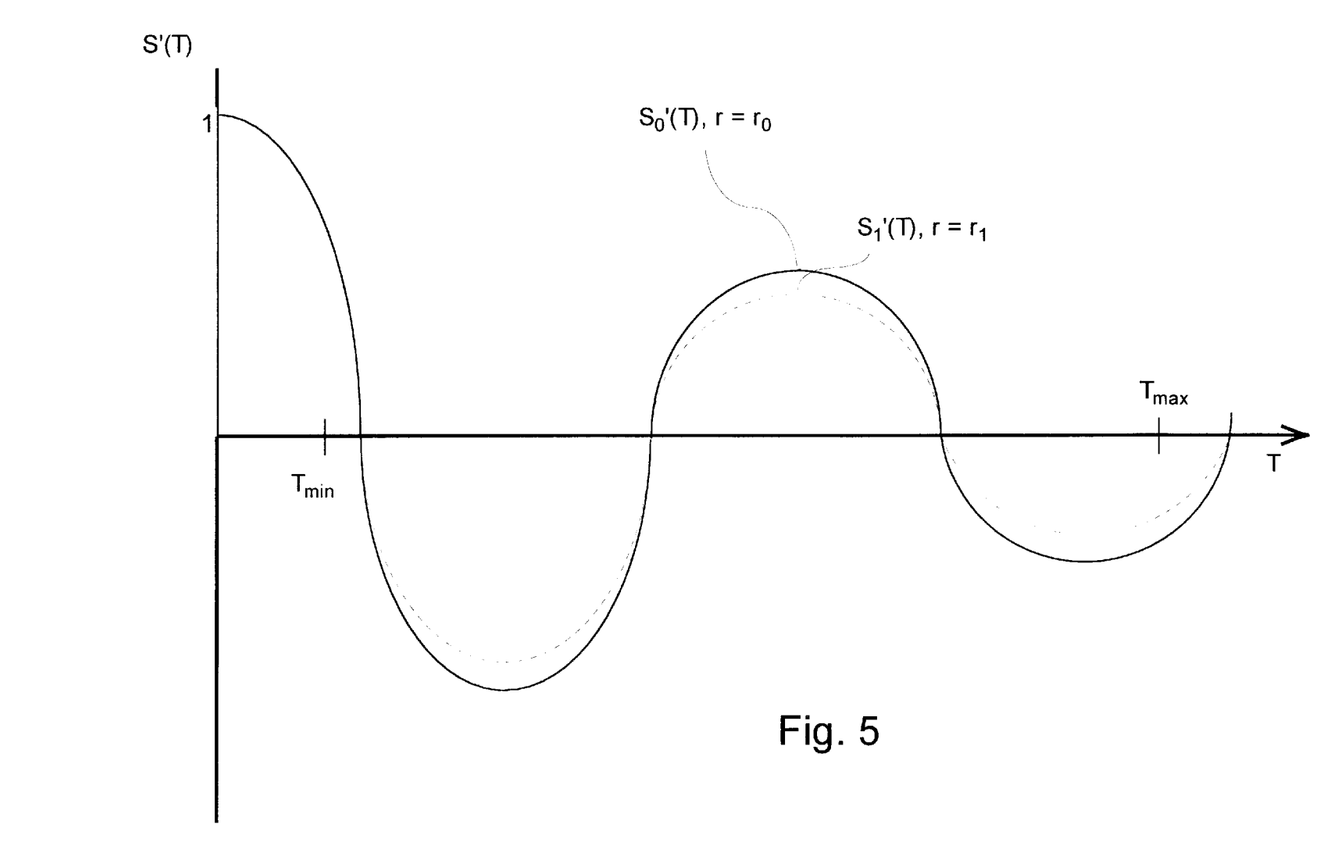
FIG. 5 is an exemplary illustration of the normalized autocorrelation function S'(T) for different values of r.

FIG. 5 is an exemplary illustration of the normalized autocorrelation function S'(T) for different values of r. It is desired to obtain the best value of r to give the best normalized autocorrelation estimate S'(T). For example, $S_0'(T)$ for $r=r_0$ yields a better result than $S_1'(T)$ for $r=r_1$. FIG. 5 also illustrates the minimum and maximum lags of interest, $T_{min}$ and $T_{max}$.

If s(t) has periodic components, S'(T) will have maxima for $T>T_{min}$, where $T_{min}$ is the shortest cycle interval of s(t) which is to be considered. $T_{min}$ is preferably less than the shortest pulse-to-pulse interval expected. For every useful value of T, the value of r which maximizes S'(T) is designated p(T). The corresponding value of S'(T) is designated Q(T). The solution for p(T) and Q(T) is found by setting the derivative of S'(T) with respect to r equal to zero.

For simplicity of mathematical manipulations, the following definitions are made:

$$A_1=Y(0)U(T)-U(0)Y(T) \quad \text{(Eq. 11.1)}$$

$$B_1=(Y(0)X(T)-X(0)Y(T))/(2A_1) \quad \text{(Eq. 11.2)}$$

$$C_1=(U(0)X(T)-X(0)U(T))/A_1 \quad \text{(Eq. 11.3)}$$

$$D_1=\sqrt{(B_1B_1-C_1)} \quad \text{(Eq. 11.4)}$$

$$E_1=(X(T)-2(B_1+D_1)U(T)+(B_1+D_1)^2Y(T))/(X(0)- \\ 2(B_1+D_1)U(0)+(B_1+D_1)^2Y(0)) \quad \text{(Eq. 11.5)}$$

$$F_1=(X(T)-2(B_1-D_1)U(T)+(B_1-D_1)^2Y(T))/(X(0)- \\ 2(B_1-D_1)U(0)+(B_1-D_1)^2Y(0)) \quad \text{(Eq. 11.5)}$$

For $E_1>F_1$:

$$p(T)=B_1+D_1 \quad \text{(Eq. 12.1)}$$

$$Q(T)=E_1 \quad \text{(Eq. 13.1)}$$

For $E_1 < F_1$:

$$p(T) = B_1 - D_1 \quad \text{(Eq. 12.2)}$$

$$Q(T) = F_1 \quad \text{(Eq. 13.2)}$$

The noise absorption ratio, r, is then equal to $p(T_0)$, where $T_0$ is the lag for which $Q(T)$ reaches its maximum on the interval $[T_{min}, T_{max}]$. The arterial blood absorption ratio, R, is found by using Eq. 7 with T=0:

$$R = (X(0) - rU(0))/(U(0) - rY(0)) \quad \text{(Eq. 14)}$$

A transform of S'(T) may be used in place of S'(T). An example would be the Fourier transform, which would replace S'(T) by a function of frequency. Similar to the maximization of S'(T), the Fourier transform might be maximized as a function of frequency with respect to the noise absorption ratio. Moreover, the transformed function may be determined directly from x(t) and y(t) without explicit determination of either S(T) or S'(T).

A third solution for determining R and r involves taking $r = p(T_{RR})$, where $T_{RR}$ is the best estimate of the pulse-to-pulse interval. This best estimate may be taken from external information (such as ECG information), derived from available pulse oximetry data, or taken from any other available source. The arterial blood absorption ratio, R, is then found using Eq. 14.

A measure of the quality of any of the above solutions for the signal and noise absorption ratios is the mean-square signal to mean-square noise ratio, which is $S(0)/N(0)$. Generally, it suffices to select the solution with the highest signal to noise ratio. However, under some circumstances, this solution may be unphysical, or otherwise improbable. In such a case, the solution with the next highest signal-to-noise ratio may be selected.

Figure 6:
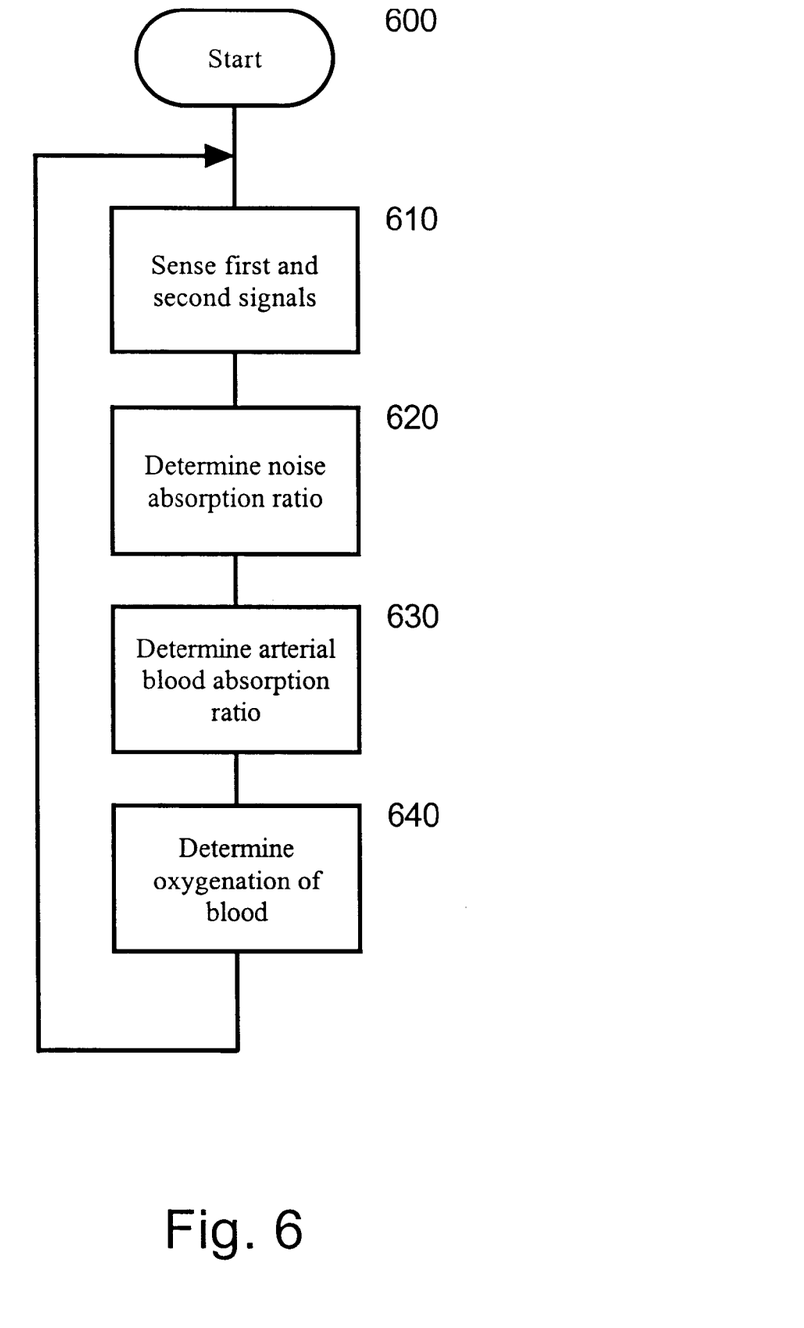
FIG. 6 is an exemplary flowchart outlining the operation of the system according to one embodiment.

FIG. 6 is an exemplary flowchart outlining the operation of the system 100 according to one embodiment in implementing the above described processes. In step 600, the operation begins. In step 610, the detectors 120 and/or 125 sense a first signal of a first wavelength, the first signal having a first arterial blood component and a first noise component. In step 610, the detectors 120 and/or 125 also sense a second signal of a second wavelength, the second signal having a second arterial blood component and a second noise component. The first arterial blood component is related to the second arterial blood component by an arterial blood absorption ratio and the first noise component is related to the second noise component by a noise absorption ratio.

In step 620, the controller 150 determines a value of the noise absorption ratio that maximizes the magnitude of an autocorrelation function. The controller 150 can maximize the magnitude of the autocorrelation function by setting a derivative of the autocorrelation function with respect to the noise absorption ratio to zero. The controller 150 can also determine the value of the noise absorption ratio by minimizing the mean square of the derivative of the autocorrelation function with respect to the noise absorption ratio and with respect to the arterial blood absorption ratio.

The controller 150 can additionally determine the value of the noise absorption ratio by determining a normalized autocorrelation function, and determining the value of the noise absorption ratio at a lag where the normalized autocorrelation function reaches a maximum on a specified interval. The normalized autocorrelation function can be determined by dividing the autocorrelation function by the autocorrelation function at a time lag of zero. The controller 150 can further determining the value of the noise absorption ratio by determining the best estimate of a pulse-to-pulse interval from either external information or information determined from available pulse oximetry data.

In step 630, the controller 150 determines the arterial blood absorption ratio from the noise absorption ratio. In step 640, the controller 150 determines the oxygenation of blood from the arterial blood absorption ratio. The process can then return to step 610 for additional processing.

The controller 150 may additionally determine the quality of at least one solution of the noise absorption ratio with respect to another solution of the noise absorption ratio based on the highest signal to noise ratio choose the best solution based on the quality of the solution. This may be determined by selecting the best solution from a set of methods including a method including the step of determining the best estimate of a pulse-to-pulse interval, a method including the step of normalizing the autocorrelation function, and a method including the step of minimizing a mean square of the autocorrelation function.

While this invention has been described with specific embodiments thereof, it is evident that many alternatives, modifications, and variations will be apparent to those skilled in the art. For example, various like aspects of various described embodiments may be combined with other like aspects of other described embodiments. Accordingly, the preferred embodiments of the invention as set forth herein are intended to be illustrative, not limiting. Various changes may be made without departing from the spirit and scope of the invention.

What is claimed is:

1. A method for determining the oxygenation of blood comprising:

sensing a first signal of a first wavelength, the first signal having a first arterial blood component and a first noise component;

sensing a second signal of a second wavelength, the second signal having a second arterial blood component and a second noise component, the first arterial blood component being related to the second arterial blood component by an arterial blood absorption ratio and the first noise component being related to the second noise component by a noise absorption ratio;

determining a value of the noise absorption ratio that maximizes the magnitude of an autocorrelation function; and determining the oxygenation of blood from the noise absorption ratio.

2. The method for determining the oxygenation of blood according to claim 1, wherein the determining the oxygenation of blood step further comprises determining the arterial blood absorption ratio from the noise absorption ratio and the determining the oxygenation of blood step comprises determining the oxygenation of blood from the arterial blood absorption ratio that is determined from the noise absorption ratio.

3. The method for determining the oxygenation of blood according to claim 2, wherein the determining the value of the noise absorption ratio step further comprises maximizing the magnitude of the autocorrelation function by setting a derivative of the autocorrelation function with respect to the noise absorption ratio to zero.

4. The method for determining the oxygenation of blood according to claim 1, wherein the determining the value of the noise absorption ratio step further comprises determining the value of the noise absorption ratio by minimizing the mean square of the derivative of the autocorrelation function with respect to the noise absorption ratio and with respect to the arterial blood absorption ratio.

5. The method for determining the oxygenation of blood according to claim 1, wherein the determining the value of the noise absorption ratio step further comprises
   determining a normalized autocorrelation function, and
   determining the value of the noise absorption ratio at a lag where the normalized autocorrelation function reaches a maximum on a specified interval.

6. The method for determining the oxygenation of blood according to claim 5, wherein the determining the normalized autocorrelation function step comprises dividing the autocorrelation function by the autocorrelation function at a time lag of zero to obtain the normalized autocorrelation function.

7. The method for determining the oxygenation of blood according to claim 1, wherein the determining the value of the noise absorption ratio step further comprises determining a best estimate of a pulse-to-pulse interval.

8. The method for determining the oxygenation of blood according to claim 7, wherein the best estimate of a pulse-to-pulse interval is determined from at least one of external information and information determined from available pulse oximetry data.

9. The method for determining the oxygenation of blood according to claim 1, further comprising:
   determining a quality of at least one solution of the noise absorption ratio with respect to another solution of the noise absorption ratio based on the highest signal to noise ratio; and
   choosing the best solution based on the quality of the solution.

10. An apparatus for determining the oxygenation of blood comprising:
    a detector configured to sense a first signal of a first wavelength, the first signal having a first arterial blood component and a first noise component, the detector also configured to sense a second signal of a second wavelength, the second signal having a second arterial blood component and a second noise component, the first arterial blood component being related to the second arterial blood component by an arterial blood absorption ratio and the first noise component being related to the second noise component by a noise absorption ratio; and
    a controller configured to determine a value of the noise absorption ratio that maximizes the magnitude of an autocorrelation function and configured to determine the oxygenation of blood from the noise absorption ratio.

11. The apparatus for determining the oxygenation of blood according to claim 10, wherein the controller is further configured to determine the oxygenation of blood by determining the arterial blood absorption ratio from the noise absorption ratio and determining the oxygenation of blood from the arterial blood absorption ratio determined from the noise absorption ratio.

12. The apparatus for determining the oxygenation of blood according to claim 11, wherein the controller is further configured to determine the value of the noise absorption ratio by maximizing the magnitude of the autocorrelation function by setting a derivative of the autocorrelation function with respect to the noise absorption ratio to zero.

13. The apparatus for determining the oxygenation of blood according to claim 10, wherein the controller is further configured to determine the value of the noise absorption ratio by minimizing the mean square of the derivative of the autocorrelation function with respect to the noise absorption ratio and with respect to the arterial blood absorption ratio.

14. The apparatus for determining the oxygenation of blood according to claim 10, wherein the controller is further configured to determine the value of the noise absorption ratio by determining a normalized autocorrelation function and determining the value of the noise absorption ratio at a lag where the normalized autocorrelation function reaches a maximum on a specified interval.

15. The apparatus for determining the oxygenation of blood according to claim 14, wherein the controller is further configured to determine the normalized autocorrelation function by dividing the autocorrelation function by the autocorrelation function at a time lag of zero to obtain the normalized autocorrelation function.

16. The apparatus for determining the oxygenation of blood according to claim 10, wherein the controller is further configured to determine the value of the noise absorption ratio by determining a best estimate of a pulse-to-pulse interval.

17. The apparatus for determining the oxygenation of blood according to claim 16, wherein the best estimate of a pulse-to-pulse interval is determined from at least one of external information and information determined from available pulse oximetry data.

18. The apparatus for determining the oxygenation of blood according to claim 10, wherein the controller is further configured to determine the quality of at least one solution of the noise absorption ratio with respect to another solution of the noise absorption ratio based on the highest signal-to-noise ratio and configured to choose the best solution based on the quality of the solution.

19. A pulse oximeter comprising:
    a light source configured to provide first signal of a first wavelength and a second signal of a second wavelength;
    a detector configured to sense the first signal of the first wavelength, the first signal having a first arterial blood component and a first noise component, the detector also configured to sense the second signal of the second wavelength, the second signal having a second arterial blood component and a second noise component, the first arterial blood component being related to the second arterial blood component by an arterial blood absorption ratio and the first noise component being related to the second noise component by a noise absorption ratio;
    a processor configured to determine a value of the noise absorption ratio that maximizes the magnitude of an autocorrelation function and configured to determine the oxygenation of blood from the noise absorption ratio.

20. The pulse oximeter according to claim 19, wherein the processor is further configured to determine the oxygenation of blood by determining the arterial blood absorption ratio from the noise absorption ratio and determining the oxygenation of blood from the arterial blood absorption ratio.

21. The pulse oximeter according to claim 20, wherein the processor is further configured to determine the value of the noise absorption ratio by maximizing the magnitude of the autocorrelation function by setting a derivative of the autocorrelation function with respect to the noise absorption ratio to zero.

22. A method for determining the oxygenation of blood comprising:
    transmitting a signal through a medium containing blood;
    sensing a first signal of a first wavelength, the first signal having a first arterial blood component and a first noise component;

sensing a second signal of a second wavelength, the second signal having a second arterial blood component and a second noise component, the first arterial blood component being related to the second arterial blood component by an arterial blood absorption ratio and the first noise component being related to the second noise component by a noise absorption ratio;

determining a value of the noise absorption ratio that maximizes the magnitude of an autocorrelation function; and determining the oxygenation of blood from the noise absorption ratio.

23. The method for determining a oxygenation of blood according to claim 22, further comprising:

determining a quality of at least one solution of the noise absorption ratio with respect to another solution of the noise absorption ratio based on the highest signal to noise ratio; and choosing the best solution based on the quality of the solution.

24. The method for determining the oxygenation of blood according to claim 23, wherein the at least one solution comprises a method including the step of minimizing a mean square of the autocorrelation function and the another solution comprises a method including the step of normalizing the autocorrelation function.

25. The method for determining the oxygenation of blood according to claim 23, wherein the at least one solution comprises a method including the step of minimizing a mean square of the autocorrelation function and the another solution comprises a method including the step of determining the best estimate of a pulse-to-pulse interval.

26. The method for determining the oxygenation of blood according to claim 23, wherein the at least one solution comprises a method including the step of normalizing the autocorrelation function and the another solution comprises a method including the step of determining the best estimate of a pulse-to-pulse interval.

27. The method for determining the oxygenation of blood according to claim 23, wherein the at least one solution is calculated by:

a method including the step of determining the best estimate of a pulse-to-pulse interval;

a method including the step of normalizing the autocorrelation function; or a method including the step of minimizing a mean square of the autocorrelation function.

28. An apparatus for determining the oxygenation of blood comprising:

a transmitter configured to transmit a signal through a medium containing blood;

a detector configured to sense a first signal of a first wavelength, the first signal having a first arterial blood component and a first noise component, the detector also configured to sense a second signal of a second wavelength, the second signal having a second arterial blood component and a second noise component, the first arterial blood component being related to the second arterial blood component by an arterial blood absorption ratio and the first noise component being related to the second noise component by a noise absorption ratio; and a controller configured to determine a value of the noise absorption ratio that maximizes the magnitude of an autocorrelation function and configured to determine the oxygenation of blood from the noise absorption ratio.

29. The apparatus for determining the oxygenation of blood according to claim 28, wherein the controller is further configured to determine the quality of at least one solution of the noise absorption ratio with respect to another solution of the noise absorption ratio based on the highest signal-to-noise ratio and configured to choose the best solution based on the quality of the solution.

30. The apparatus for determining the oxygenation of blood according to claim 29, wherein the controller is further configured to obtain the at least one solution by determining the best estimate of a pulse-to-pulse interval, normalizing the autocorrelation function, or minimizing a mean square of the autocorrelation function.

* * * * *